United States Patent [19]

Panetta et al.

[11] Patent Number: 4,599,738
[45] Date of Patent: Jul. 8, 1986

[54] UNIVERSAL MAMMOGRAPHY COMPRESSION SYSTEM

[76] Inventors: Patrick Panetta, 29 Keswick Dr., East Islip, N.Y. 11730; Jack Wennet, 20 Spinner La., Commack, N.Y. 11725

[21] Appl. No.: 601,279

[22] Filed: Apr. 17, 1984

[51] Int. Cl.$^4$ .............................................. G03B 41/16
[52] U.S. Cl. ..................................... 378/037; 378/180
[58] Field of Search ............... 378/037, 177, 196, 195, 378/179, 180

[56] References Cited

U.S. PATENT DOCUMENTS 3,824,397 7/1974 Bauer et al. ........................... 378/37

Primary Examiner—Alfred E. Smith
Assistant Examiner—T. N. Grigsby
Attorney, Agent, or Firm—Lackenbach Siegel Marzullo Presta & Aronson

[57] ABSTRACT

A mammography compression system provides for both non-magnification compression examination as well as magnification compression examination through a large plurality of positions whereby the patient may remain seated upright or standing. The system permits utilization of a radiologist's present in place X-ray equipment and readily mounts for juxtaposition with the existing in place x-ray system.

15 Claims, 11 Drawing Figures

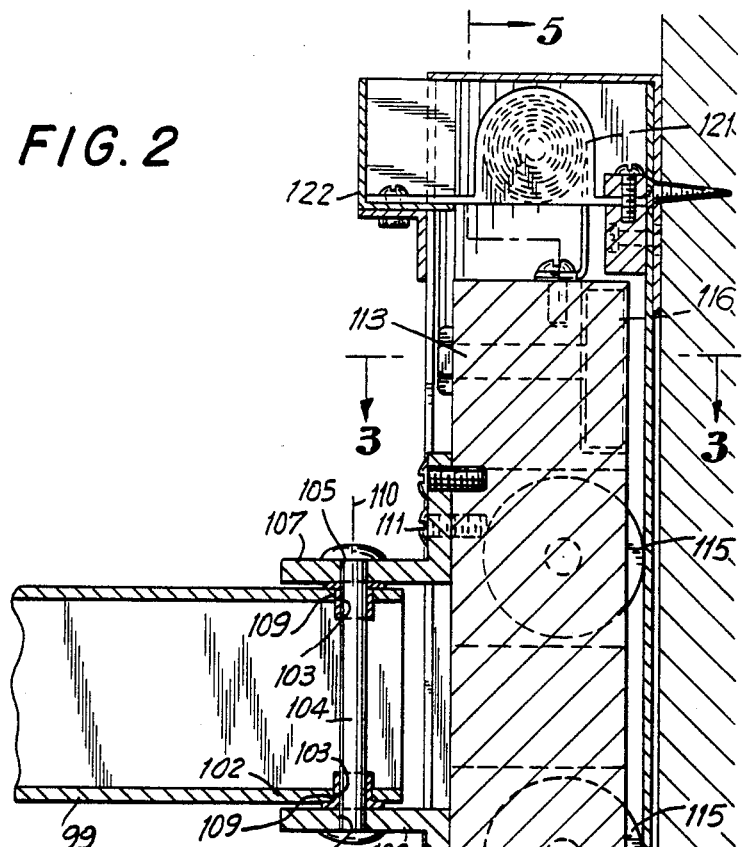
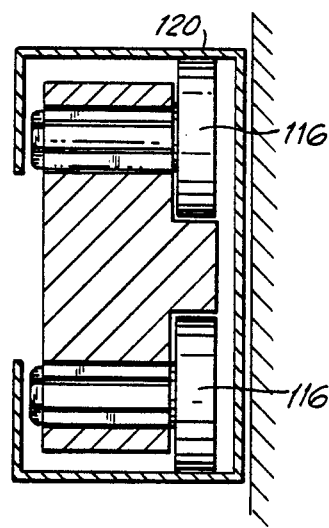
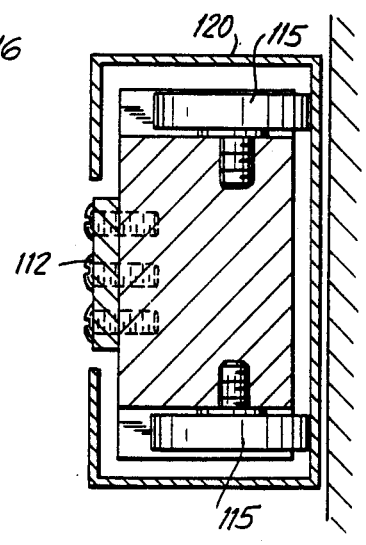

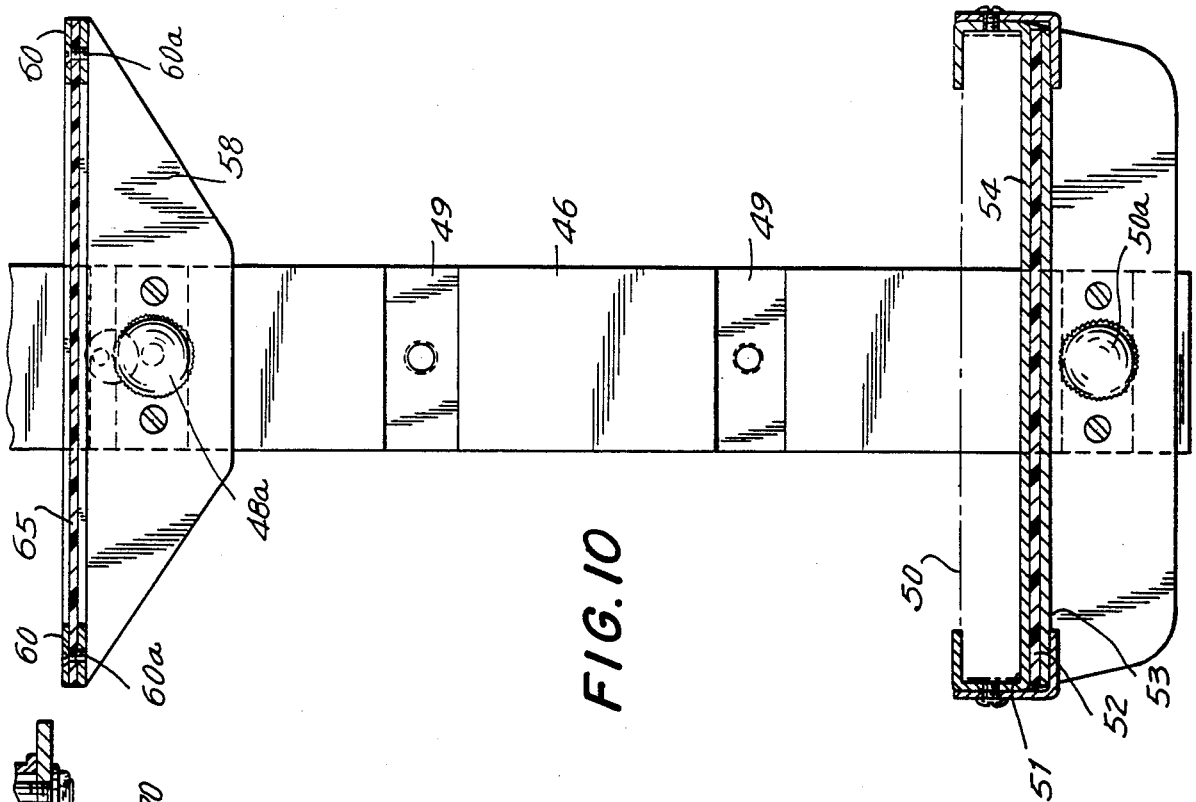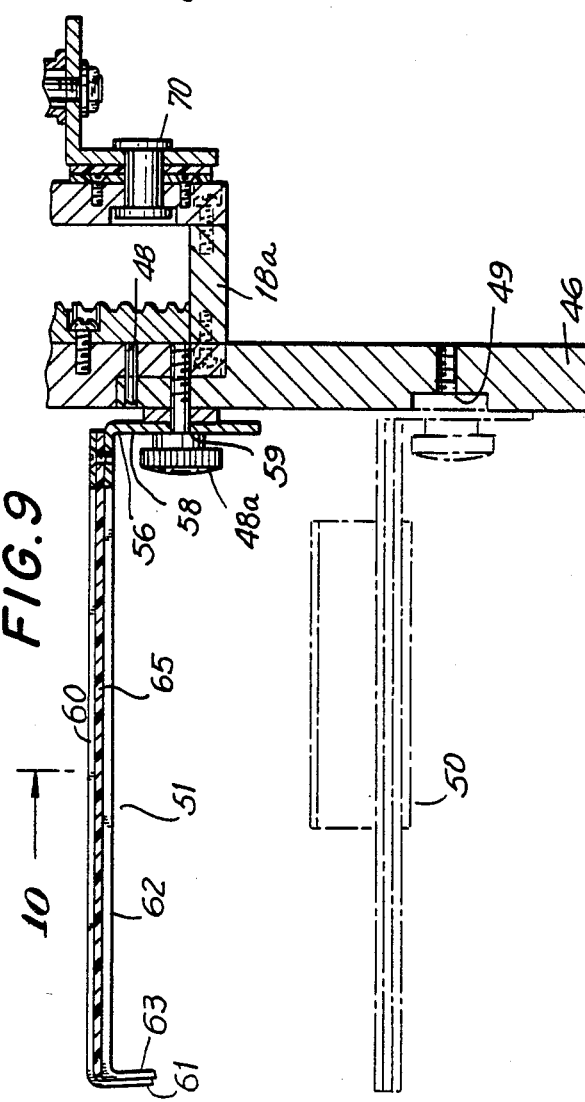

4,599,738

UNIVERSAL MAMMOGRAPHY COMPRESSION SYSTEM

FIELD OF THE INVENTION

This invention relates to compression mammography. Specifically, this invention relates to a system for universal positioning for compression mammography.

BACKGROUND AND DISCUSSION OF THE PRIOR ART

In the field of compression mammography, the breast is compressed between plates and the X-ray taken. It is necessary to provide several angular compression positions, as well as providing for degrees of magnification to obtain a thorough examination. Generally, with prior art compression devices, the patient would have to assume diverse, uncomfortable positions in order to obtain this full series of X-rays. Further, the diverse existing in-place mounted X-ray emmission equipment impairs the radiologist or technician in multiply positioning the patient within the relative fixed geometry offered by existing in-place X-ray devices.

Specifically, in Lasky, U.S. Pat. No. 3,578,971, there is disclosed the gravitational suspension of the breast between compression plates, and in Redington et al. U.S. Pat. No. 3,973,126 there is disclosed a supine patient support and pivoting device in conjunction with built-in X-ray unit.

Now there is provided by the present invention a compression mammography system in which a full multi-positioned series of X-ray shots, including magnification shots, is available while the patient remains seated or standing.

SUMMARY OF THE INVENTION

A mammography compression system having breast support and compression elements for magnification and non-magnification X-rays through diverse angular and translation portions so as to accomodate the user in an upright position while utilizing the existing in-place X-ray generator of the radiologist.

DESCRIPTION OF THE DRAWINGS

FIG. 2 is an enlarged sectional view taken along line 2—2 of FIG. 1;

FIG. 3 is a sectional view taken along line 3—3 of FIG. 2;

FIG. 4 is a sectional view taken along line 4—4 of FIG. 2;

FIG. 9 is an enlarged partial sectional view taken along line 9—9 of FIG. 1;

FIG. 10 is a partial sectional view taken along line 10—10 of FIG. 9; and

DESCRIPTION OF THE PREFERRED EMBODIMENTS

Figure 1:
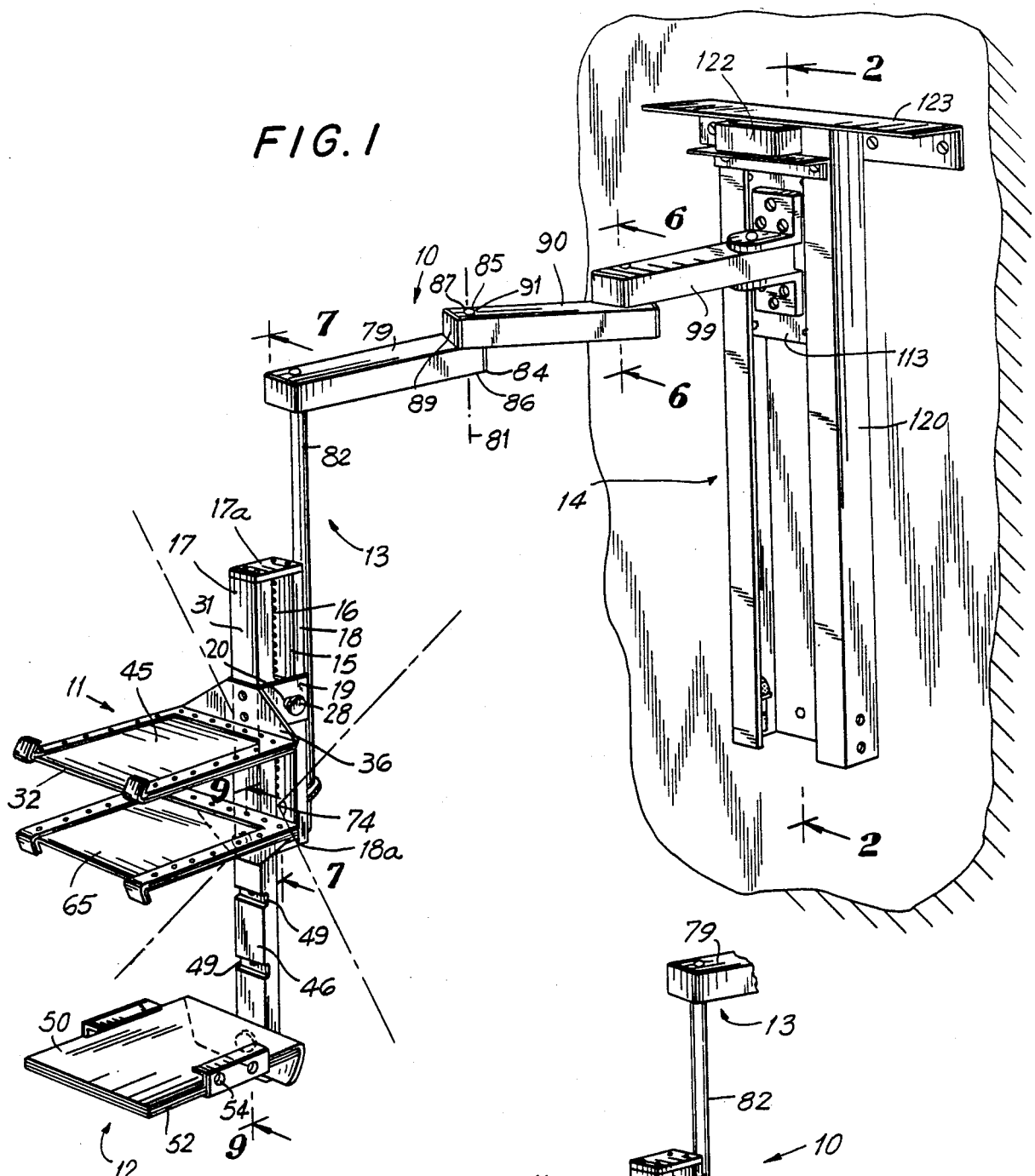
FIG. 1 is a perspective view of the mammography system of the present invention in the magnification X-ray mode.

Referring to the FIGURES, there is shown the system of the present invention generally referred to as 10. System 10 in broad terms is formed of a breast examination support section 11, an X-ray plate mount section 12, arm mount assembly 13 and a fixed support attachment assembly 14.

Breast examination support system 11 is formed with central housing 15 having a gear rack 16 vertically mounted therein and held in place between front and back members 17 and 18 and upper and lower crossbars 17a and 18b respectively. A sleeve 19 is mounted on and slidably disposed with relation to housing 15. Sleeve 19 is formed with through hole 20 which receives shaft 21 carrying spur gear 22, bushings 23, 24 and 25, set screw collars 26 and 27 and manual compression adjustment knob 28. Spur gear 22 is sized and aligned to engage teeth 29. With the turning of knob 28, gear 22 engages rack 16 so as to cause sliding movement of sleeve 19 relative to housing 15. A Delrin plastic slide plate 30 is mounted adjacent front wall 31 to facilitate sliding movement of the sleeve relative to the housing.

Upper compression plate assembly 32 is mounted to front wall 31 of sleeve 19 for movement with sleeve 19. Assembly 32 is formed of compression frame 35 having a rear mounting flange 36 mounted to wall 31 as at 37, and a pair of outwardly disposed fingers 38 having upwardly bent outward ends 39. A pair of retainer fingers or strips 40 with upwardly bent ends 41 are connected to fingers 38 through coincident holes mounting elements 42 with a transparent compression plate 45 fixedly held between fingers 38 and strips 40, for purposes hereafter appearing.

Plate 45 is formed of a polycarbonate, preferrably Lexan, and importantly, is only 0.030–0.040 inches in thickness. Prior art compression plates were undesirably 0.060 to 0.5 inch in thickness.

An elongated positioning bar 46 is formed with an alignment hole 47 for receiving alignment pin 48 at the lower end of housing 15 as well as screw mounting elements 48a. A series of vertically spaced holder mount slots 49 are provided in bar 46. Each slot 49 is sized to removably mount an X-ray plate assembly 50 for magnification shots. X-ray plate assembly 50 is formed of conventional X-ray plate 52, integrally mounted with a cover 53 and holder 54. A mounting screw 50a holds assembly 50 to bar 46.

Lower compression plate assembly 51 is mounted (for magnification X-ray) to the alignment pin 48 and through mounting screw 48a to the positioning bar 46. Lower compression plate assembly 51 is formed of compression frame 56 having a rear mounting flange 58 with hole 59 for alignment with screw 48a, and a pair of outwardly disposed fingers 60 having downwardly bent outward ends 61. A pair of retainer strips or fingers 62 formed with downwardly bent ends 63 are connected to fingers 60 through coincident mounting elements 64 with a transparent plastic compression plate 65 fixedly held between fingers 60 and strips 62 by elements 60a. Plate 65 may be similarly sized as plate 45.

Figure 11:
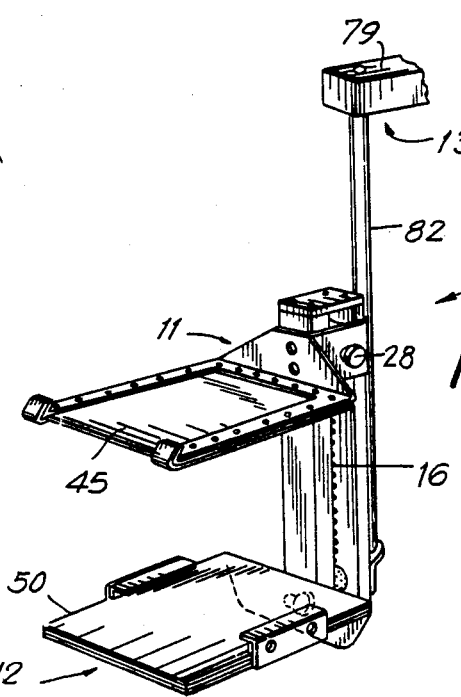
FIG. 11 is a partial perspective view of the mammography system of the present invention in the non-magnification X-ray mode.
Figure 5:
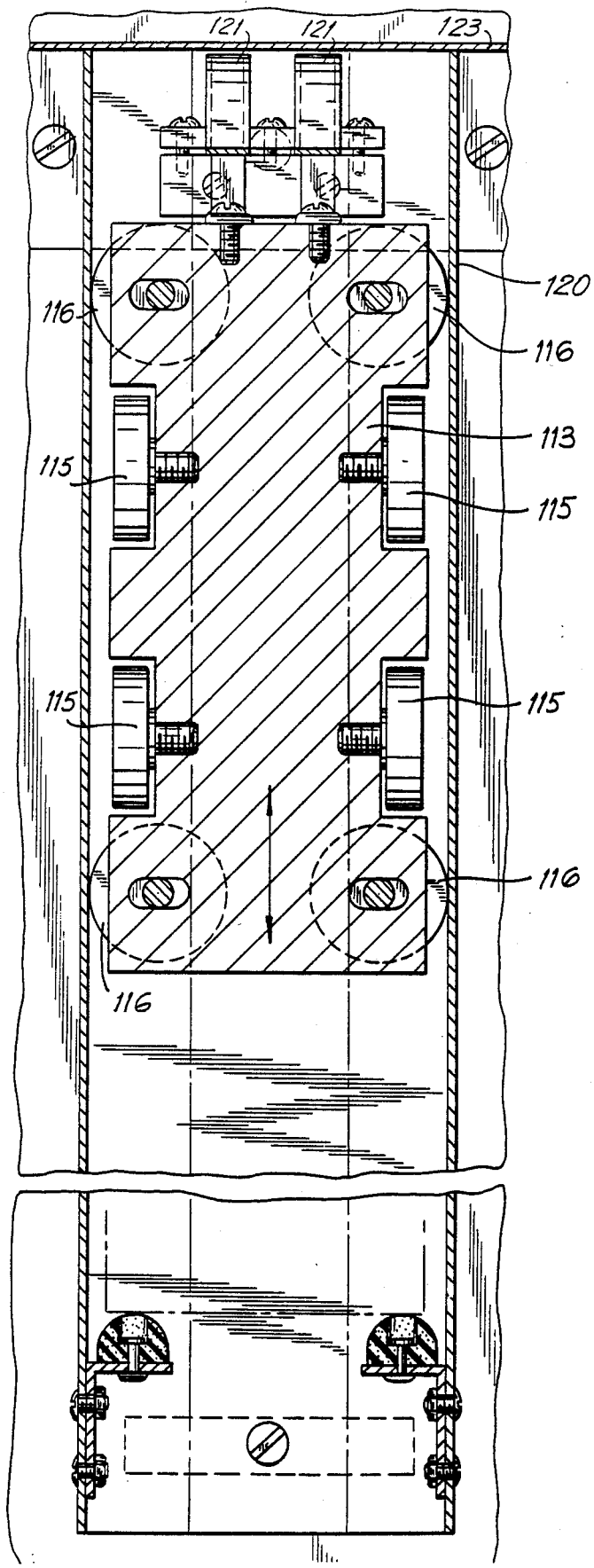
FIG. 5 is an enlarged sectional view taken along line 5—5 of FIG. 2.

For non-magnification X-rays, bar 46 and lower compression plate assembly 51 are removed, and X-ray plate assembly 50 directly mounted to alignment pin 48 (FIG. 11).

The rear wall 68 of housing 15 is provided with a pivot or rotation assembly 70 having a pivot pin 71 mounted in rotation housing elements 72 and L-flange 73 to provide a pivot axis 74. Section 11 may thereby be pivoted to the desired angle. A vertical rod or cylindrical bar 75 is mounted at one end 26 to flange 73 and the other end 77 to end 78 of first arm 79. End 77 is mounted with jam nut 80 to permit rotation of the bar 75 and in turn breast examination section 11 about the rotation axes of the arms (e.g., axis 81 of the first arm 79). Axis 81 is perpendicular to axis 74. A sleeve 82 is slidably fitted over bar 75 and is sized and formed so as to be held by the patient during examination.

Figure 6:
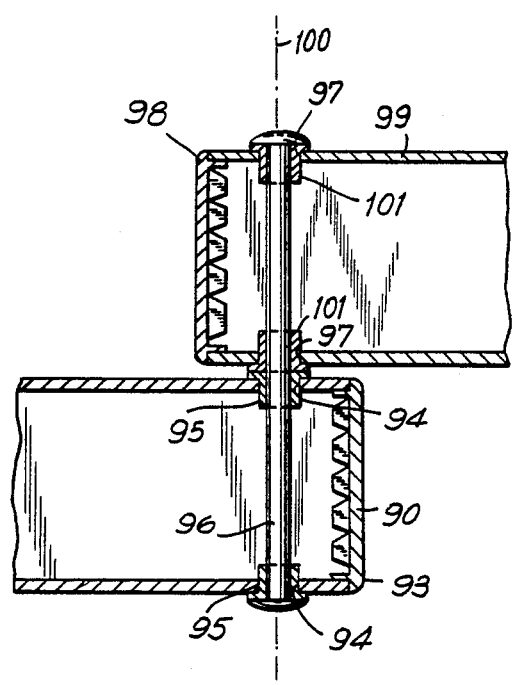
FIG. 6 is an enlarged partial sectional view taken along line 6—6 of FIG. 1.
Figure 8:
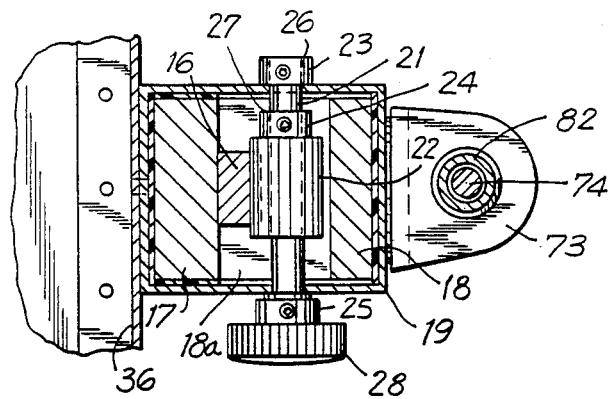
FIG. 8 is a partial sectional view taken along line 8—8 of FIG. 7.
Figure 7:
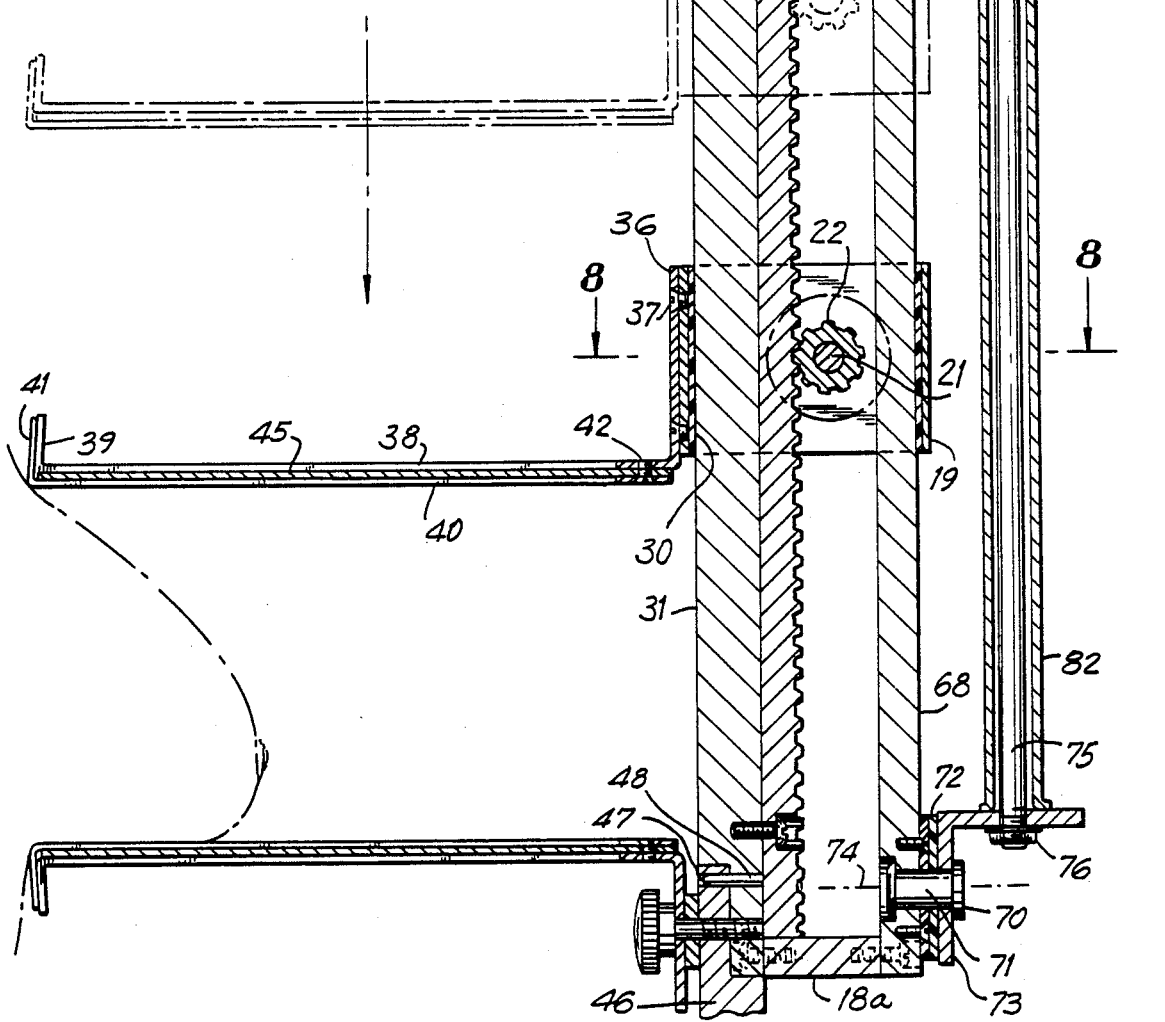
FIG. 7 is an enlarged sectional view taken along line 7 of FIG. 1 showing the action of the compression plates in compressing a breast.

First arm 79 is formed at its rearward end 84 with through hole 85 and bushings 86 for receiving rod 87. Rod 87 in turn passes through hole 88 at the forward end 89 of second arm 90, with bushings 91 completing the assembly for providing pivot axis 81. Second arm 90 is formed at its rearward end 93 with through hole 94 and bushings 95 for receiving rod 96, which rod extends upwardly through hole 97 at the forward end 98 of third arm 99 to provide pivot 100. Bushings 101 complete the assembly. FIG. 6 shows the second and third arm connection which is similar to the first and second arm connection.

The rearward end 102 of third arm 99 is formed with through hole 103 for receiving rod 104. Rod 104 also passes through holes 105 and 106 of opposed L-flanges 107 and 108 respectively. Bushings 109 complete this assembly to provide pivot axis 110. L-flanges 107 and 108 are mounted at 111 and 112 to vertical trolley assembly 113 of attachment assembly 14. Trolley assembly 113 is formed with radial bearings 115 and lateral bearings 116 so as to be slidably received in wall mount C-channel 120. A pair of conventional constant pull spring counterbalances 121 are mounted to the trolley assembly 113 and to the C-channel 120 to provide the trolley with vertical reciprocal travel in the C-channel to any desired height. A spring assembly cover 122 completes the assembly.

Attachment assembly 14 may be wall mounted as shown in FIG. 1, or an attachment bracket 123 provided for ceiling mount.

By the aforesaid manner of construction, the breast examination support unit, for either magnification or non-magnification X-ray may be rotated about axes 74 and 81, as well as 100 and 110 and also being translationally moved through pivot arms or linkages 79, 90 and 99 and raised or lowered through trolley 113, to the desired position for the specifically desired X-ray angle. The patient's breast is then placed between the upper compression plastic plate 45 and either the lower compression plastic plate 65 (magnification) or the X-ray plate assembly (non-magnification) 50 and the upper plate 45 lowered by knob 28 to compress the breast. With the breast compressed, the X-ray technician then aligns the existing X-ray generator with the afore-discussed universal system. All the aforesaid movements and alignments may be accomplished with the patient in an upright seated or standing position. The patient may then extend her arms and grasp sleeve 82 with her hands for ease in taking the X-ray. In using the present system, there is no need for the patient to assume a supine position.

It is to be noted that the several pivot and translation movements of the present system permit the breast examination support section to fully translate a volume of at least more than a quadrant of a cylinder.

It is also noted that the dial knob, spur gear and gear rack assembly permits compression of the breast in a locked position with exertion of counter-forces of the compressed breast on the upper plate.

The system design of the present invention permits utilization of thinner compression plates than heretofore with concommitant improvement in X-ray transmission.

The afore-described universal positioning system permits the patient to remain seated or standing upright during a full series of X-rays.

The invention has been described in detail herein in accord with certain embodiments thereof, yet many modifications and changes therein may be effected by those skilled in the art. Accordingly, it is intended by the appended claims to cover all such modifications and changes as fall within the true spirit and scope of the invention.

What is claimed is:

1. A mammography compression system for a patient comprising; breast examination support means having opposed upper and lower compression plate mounts and compression plates disposed in said mounts, for compressing the breasts of a patient therebetween; said breast examination support means further comprising an X-ray plate mount for mounting an X-ray plate in a plurality of positions relative to said upper compression plate; mounting means connected to said breast support means at an end of the mounting means; attachment means connected to another end of said mounting means for attachment to a fixed support; said mounting means comprising means for retractably and extendably moving said breast support means relative to said fixed support, and means for rotatably moving said breast examination support means; and said compression and X-ray plate mounts being formed so that said X-ray plate is mountable in said lower compression plate mount, whereby said breast examination support means is movable to several examination positions while the patient remains substantially upright, and with the use of said compression plates and said X-ray plate, there is a magnification X-ray and with the upper compression plate and said X-ray plate in the lower compression plate position, there is a non-magnification compression X-ray.

2. The mammography compression system of claim 1, said upper compression plate mount further comprising means to vertically move said mount.

3. The mammography compression system of claim 1, each said plate mount being formed with pairs of spaced, parallel outwardly extending fingers, and wherein the outward ends of the fingers of said upper mount being upwardly bent and the outward ends of said lower mount being downwardly bent.

4. The mammography compression system of claim 1, said X-ray plate mount being formed so as to be detachable from said compression plate mounts.

5. The mammography compression system of claim 1, said X-ray plate mount being an elongated member being formed with a plurality of spaced slots forming said plurality of X-ray plate mount positions.

6. The mammography compression system of claim 1, said mounting means and attachment means being formed so as to provide reciprocal vertical movement to said breast support means.

7. The mammography compression system of claim 6, said movements of said breast support means transversing a spatial volume at least equal to that of about a quadrant of a cylinder.

8. The mammography compression system of claim 1, said compression plates being transparent plastic plates.

9. The mammography compression system of claim 8, each said compression plate being no greater than about 0.040 inch in thickness.

10. The mammography compression system of claim 9, said plates being a polycarbonate.

11. The mammography compression system of claim 1, said means to rotatably move said breast support means comprising a vertical member and means to pivotally mount said breast support means about one axis perpendicular to said vertical member and about a second axis parallel to said vertical member.

12. The mammography compression system of claim 11, said vertical member extending upwardly beyond the breast support means and being formed so as to be gripped by the user during examination.

13. The mammography compression system of claim 11, said means to retractably and extendably move said breast support means comprising a plurality of arm linkages, and pivot means interconnecting said linkages.

14. The mammography compression system of claim 13, said attachment means comprising means to mount the system to a vertical wall and further comprising means to reciprocally vertically move said linkages and in turn said vertical member and breast support means.

15. The mammography compression system of claim 14, further comprising means to stop the vertical movement.

* * * * *